United States Patent [19]

Chalifoux

[11] Patent Number: 5,788,497

[45] Date of Patent: Aug. 4, 1998

[54] DENTAL POST

[75] Inventor: Paul R. Chalifoux, Wellesley, Mass.

[73] Assignee: Wellesley Research Associates, Inc., Wellesley, Mass.

[21] Appl. No.: 494,380

[22] Filed: Jun. 26, 1995

Related U.S. Application Data

[63] Continuation-in-part of Ser. No. 196,953, Feb. 15, 1994, abandoned, which is a continuation-in-part of Ser. No. 75,329, Jun. 11, 1993, Pat. No. 5,362,237, which is a continuation-in-part of Ser. No. 908,366, Jul. 6, 1992, Pat. No. 5,316,478, which is a continuation-in-part of Ser. No. 969,060, Oct. 30, 1992, Pat. No. 5,336,092, which is a continuation-in-part of Ser. No. 896,388, Jun. 10, 1992, Pat. No. 5,342,200, which is a continuation-in-part of Ser. No. 739,670, Aug. 2, 1991, Pat. No. 5,277,583.

[51] Int. Cl.$^6$ ....................................................... A61C 5/08
[52] U.S. Cl. ............................................. 433/220; 433/221
[58] Field of Search .................................. 433/165, 221, 433/220, 225

[56] References Cited

U.S. PATENT DOCUMENTS

| 756,506 | 4/1904 | Kidder. | |
|---|---|---|---|
| 1,589,994 | 6/1926 | Simmons. | |
| 4,738,616 | 4/1988 | Reynaud | 433/220 |
| 4,871,313 | 10/1989 | Maillefer | 433/225 |

FOREIGN PATENT DOCUMENTS

| 78680 | 7/1962 | France | 433/220 |
|---|---|---|---|
| 579504 | 8/1931 | Germany | 433/220 |
| 361315 | 11/1931 | United Kingdom | 433/165 |
| 391683 | 5/1933 | United Kingdom | 433/221 |
| 396973 | 8/1933 | United Kingdom | 433/221 |

*Primary Examiner*—Cary E. O'Connor
*Attorney, Agent, or Firm*—Paul J. Cook

[57] ABSTRACT

A dental post having a top section and a lower section is provided wherein the lower section has a plurality of subsections. The subsections have a progressively reduced effective diameter in vertical direction away from the top section.

9 Claims, 14 Drawing Sheets

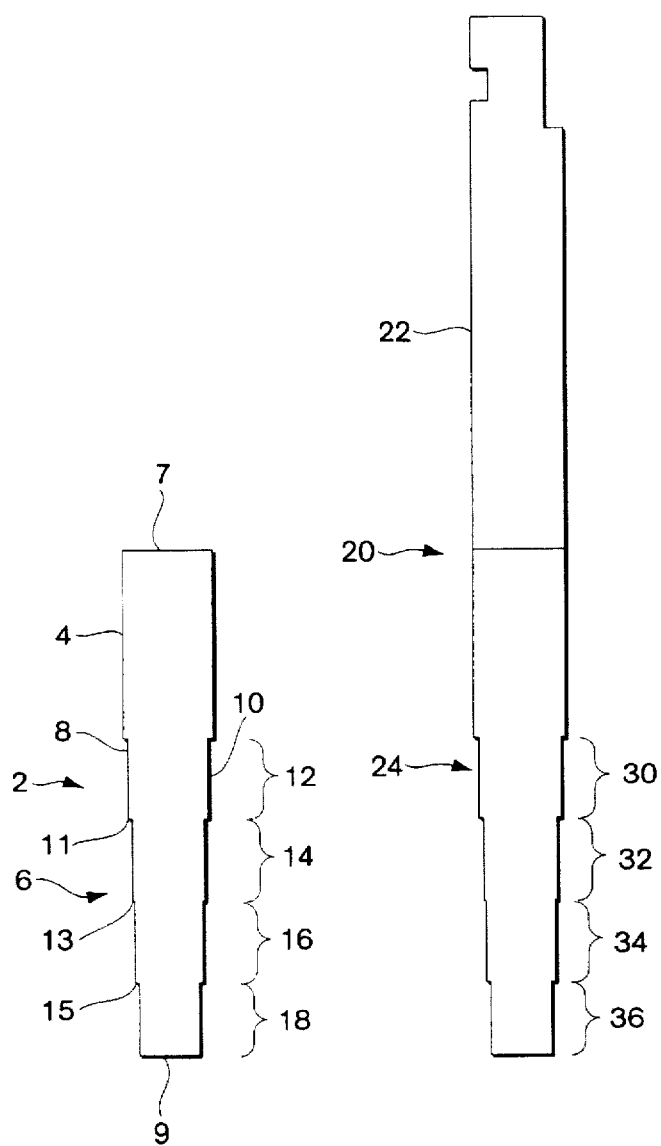
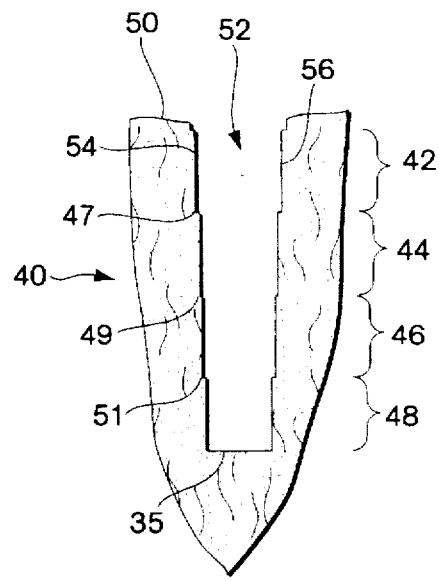
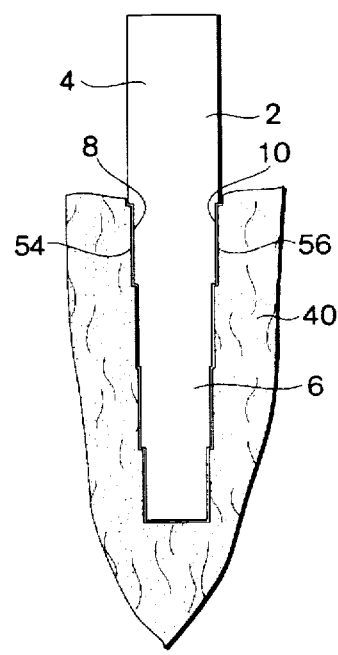
Fig. 1    Fig. 2    Fig. 3    Fig. 4

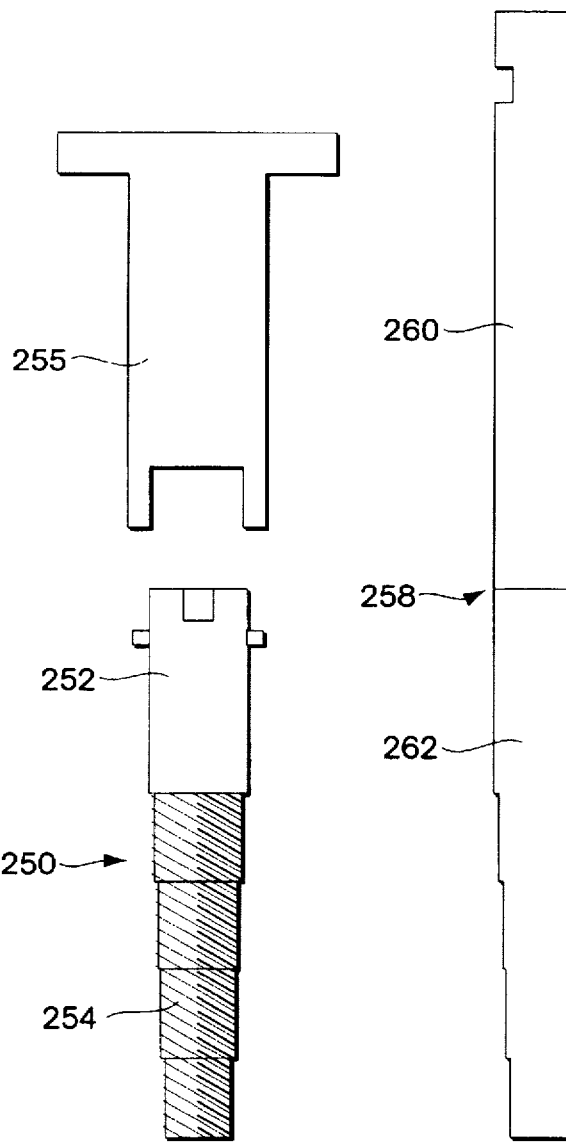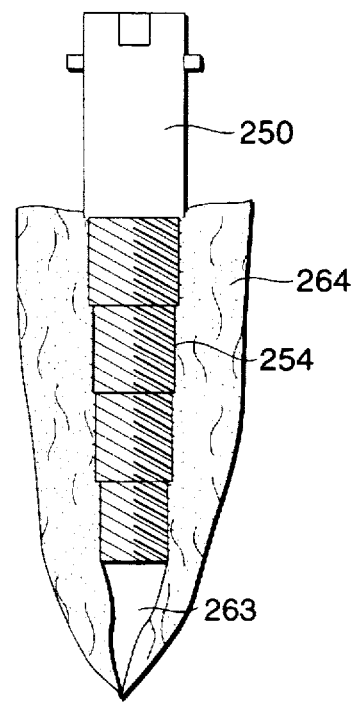
Fig. 23   Fig. 24   Fig. 25

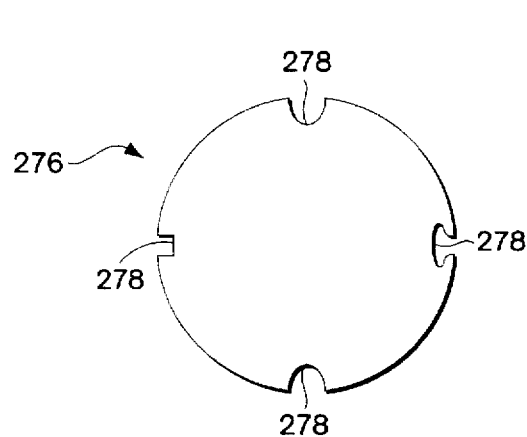
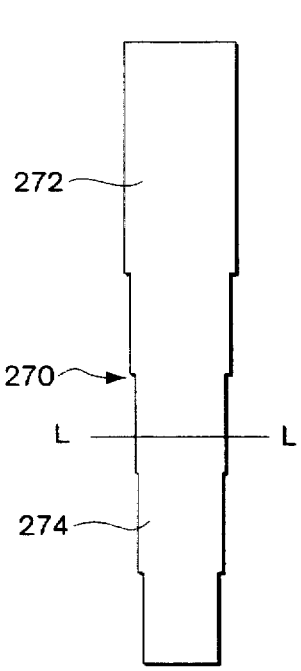
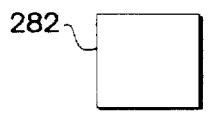
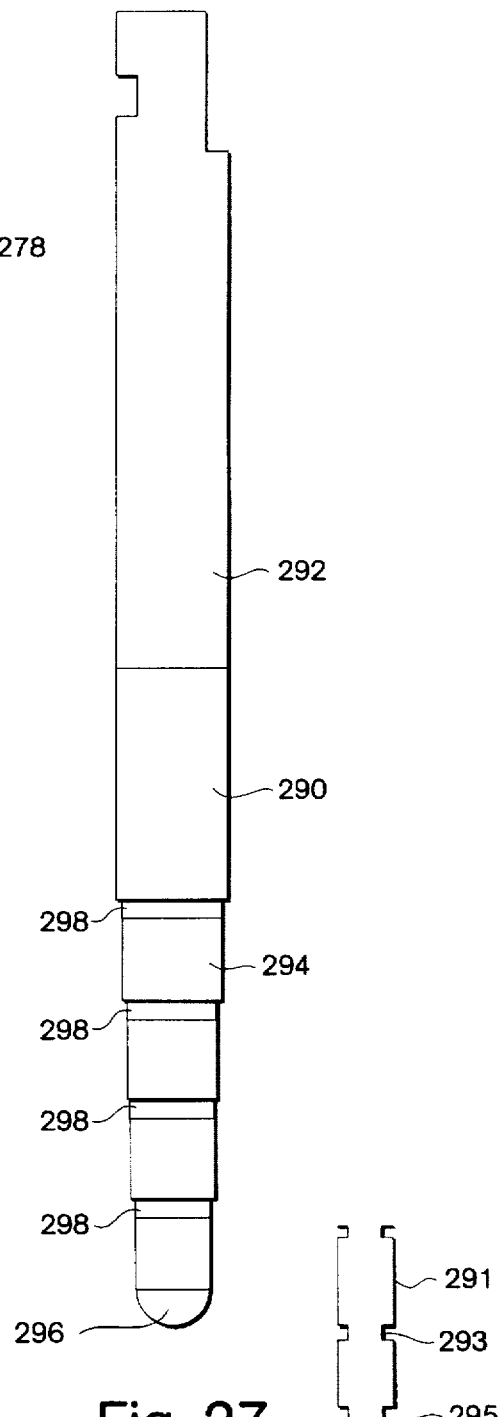
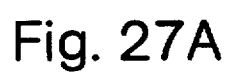

DENTAL POST

REFERENCE TO RELATED APPLICATION

This application is a continuation-in-part of Ser. No. 08/196,953, filed Feb. 15, 1994, now abandoned which in turn, is a continuation-in-part of Ser. No. 08/075,329 filed Jun. 11, 1993 now U.S. Pat. No. 5,362,237 which, in turn, is a continuation-in-part of Ser. No. 07/908,366 filed Jul. 6, 1992 now U.S. Pat. No. 5,316,478 which, in turn, is a continuation-in-part of Ser. No. 07/969,060 filed Oct. 30, 1992 now U.S. Pat. No. 5,336,092 which, in turn, is a continuation-in-part of Ser. No. 07/896,388, filed Jun. 10, 1992 now U.S. Pat. No. 5,342,200 which, in turn, is a continuation-in-part of Ser. No. 07/739,670 filed Aug. 2, 1991 now U.S. Pat. No. 5,277,583.

BACKGROUND OF THE INVENTION

This invention relates to a dental post construction which can be inserted into a tooth stub and which is utilized to improve retention of a dental restoration built onto the tooth stub.

It is present dental procedure to form a dental prosthetic structure onto a tooth stub for replacement of missing dentition. In this procedure, a tooth stub is initially prepared by removing the diseased or damaged top portion of a tooth to form a tooth stub. A base is formed by drilling into the root canal portion of the tooth stub to form a space into which a dental post can be inserted. Presently available dental post include grooves on their surface designed to improve retention of the post within the tooth stub. Dental cement is employed in the bore in conjunction with the dental post to secure the post in the tooth stub. A portion of the post extends above the tooth stub upper surface so that a dental prosthesis formed on the tooth stub can be retained.

Preformed posts are posts which are premade to specific dimensions with matching burs having cutting surfaces. The burs have a matching diameter to the post and prepare the root to accept a post. A post is then tried in the root and cut to the appropriate length. Cement is spun into the canal with a device referred to as a lenticula spiral, placed directly with a syringe and/or placed directly on the post. The post is placed in the canal and held in position until excess cement extrudes and the cement hardens. Most preformed posts require placing filling material around the top of the post to transfer strength from the post to the crown. This procedure is referred to as the core build up or post and core procedure.

There are many problems which are encountered when utilizing preformed posts. These include:

An inaccurate fit develops with present bur technology.

Potential for perforation of the root is great with present burs.

There is inadequate resistance to rotational forces on the post.

Root fracture caused by lateral stresses occurs.

There is weak transfer of strength from the post to the crown positioned on the post.

An accurately drilled hole results in good proximity of the post to the canal walls with a thin cement layer to provide greater success in properly positioning the post. The hole is inaccurate if tipping or vibrating of the bur occurs during root preparation as occurs with present drilling systems. This adds to the failure rate of preformed post systems. Drilling a straight hole for a straight post in a curved canal or drilling a hole which does not align with a canal can lead to perforation of a root and loss of a tooth. All posts must resist normal rotational forces which occur during normal or abnormal functions if there is not sufficient tooth structure to provide resistance. In general, preformed posts do not provide good stability against rotational force because they are round and rotate easily when placed in a round hole such as that provided by present bur systems. Presently, to compensate for this, a separate pin may be placed into the tooth. Some systems try to make posts oval or non-symmetrical at the top but do not supply dependable resistance and retention form. Cement merely provides suction to hold a post in position. The strength of the cement becomes a weak point to the root-post-crown relationship. Constant repeated forces of chewing causes potential breakdown on the tooth-cement-crown interface with subsequent cement wash out and crown post failure. An uneven or excessive amount force can cause root fracture and tooth loss. In addition, forceful placement of cement type posts without proper venting of cement can cause root fracture and tooth loss. Filling material is placed around a preformed post above the root to accept a crown after the post is cemented. The strength and long term stability of this material becomes a weak link in long term success of the crown. In addition, proper design of the post above the root is critical to resist rotation or dislodging of the filling material from the post.

A cast post is inducted for root canalled teeth with no clinical crown (no tooth above the height of the gums) and/or teeth with root canal spaces which are shaped in such a manner that a preformed post can not fit properly. For example, a canal may be narrow at its bottom half and diverge rapidly in the top half or it may be too oval shaped. The preformed post which is of the same diameter throughout can not accommodate these situations. When utilizing a cast post, root preparation is done by drilling to remove undercuts and obtain slight divergence from the bottom upward. The cast post technique takes an impression of a prepared root canal space. In indirect methods, an impression of the root is taken with a dental impression material. In direct methods, an acrylic pattern of the prepared root and the desired shape above the gums is achieved in the mouth. Laboratory procedures which include casting in a lost wax technique are then necessary to construct the cast post. There are many problems which are encountered when utilizing casts posts. The problems include: An increased chance of root fracture. The cast post is expensive. There is an increased possibility of root perforation. The cast post may not provide good resistance to rotational forces.

All posts need to provide venting of cement as a post is placed. A cast post is very precise fitting so it is difficult for cement to vent, lateral forces can fracture the root and/or the post will not be fully seated as excess cement remains in the bottom. In addition, any bubbles or inaccuracies from the casting process can cause a poor fit and root fracture. Cast posts dramatically increases cost as compared to preformed posts because there are laboratory fees and increased time required to treat the patient. For a cast post, an appointment is needed for an impression in addition to an appointment for post placement. The patient cost of a cast post is double the cost of a preformed post. The doctors laboratory cost may be five to ten times the cost to buy a preformed post.

Preparation of a root canal space must be free of any undercuts or removal of a cast post in its plastic or wax phase of construction will be impossible. It is often difficult to attain this as root canals tend to be complex systems of lateral canals, ribbon shapes, multiple canals, etc. Often, excessive drilling is done which removes important tooth structure and leads to a weaker root and increased chance of root fracture or perforation.

Present posts are further classified as being parallel or tapered. Parallel posts have the sides of the post parallel to each other. They form the strongest retention of any post design because the suction created is strong. However, because they are parallel and the same diameter throughout while root canal spaces are tapered, it is necessary to destroy more tooth structure than a tapered design. Tapered posts have sides angled relative to each other such that the bottom of the post has the smallest diameter. While there are less retention forces for tapered posts than parallel posts, more tooth structure is maintained which results in a stronger root. Unfortunately, tapered posts produce a wedging force when force is applied on the top of the post which results in increased root fracture.

It has been proposed in U.S. Pat. Nos. 4,480,997; 4,490,116 and Re 31,948 to utilize a threaded dental post which is introduced into the bore of a tooth stub by being rotated to thread the post into position. The dental post includes a stem portion having a slot extending through the stem thickness and along its length which renders the stem being formed of two legs each having its outside surface threaded. The outside surface of the legs intimately contact the walls of the bore so that the threads on the legs can engage the walls. In addition, a spring-like connection for the two legs is provided so that a radial outward spring force is applied to the legs to force them against the bore walls. These dental posts are undesirable since a rotational force must be applied to the post to position it properly into the bore. This positioning process is undesirable since it is time consuming and causes the patient discomfort. Furthermore, the radially outward forces of the legs on the tooth stub can result in fracture of the tooth stub over time.

U.S. Pat. No. 1,534,409 discloses a two legged post having corrugated surfaces which fit into a root canal having generally parallel walls. This surface design materially reduces the post surface area which contacts the canal walls and thus post retention relies primarily upon cement adhesive strength.

Accordingly, it would be desirable to provide a dental post which can be inserted into the bore of a tooth stub while maintaining maximum amount of tooth structure as occurs with tapered designs, but avoiding application of a wedging force and in order to obtain the retentive strength of a parallel post design. It would be further advantageous to assure a post cannot contact tooth structure in a point contact which could generate fracture forces.

SUMMARY OF THE INVENTION

This invention provides a dental post having a stem section and a lower section. The lower section is further divided into multiple sections. The sections of the lower section can be parallel sided but generally decrease in diameter from the top of the post to the bottom of the post. The bottom most section is longer than the bottom section of a matching drill. The bottom of the post will press against the bottom of the preparation and not allow ledges created by the decreasing diameter sections, to engage ledges in the root structure created by the drill preparing the root. In one embodiment, the post has venting grooves for cement to vent when placement into the root canal occurs. A matching bur is provided which shapes a hole with parallel step down into the root canal space to match the outer surface configuration of the post. In one embodiment the bur has non-cutting areas along the lower section and along the sides of the bur to provide guidance for direction during the drilling process.

The bore of the tooth stub is initially shaped with standard endodontic procedures. Endodontic filling material is removed and the canal is shaped with a bur. The bur is shaped with at least two sections but as many as about twenty sections can be utilized, such that each section has parallel walls and each section decreases in size in a downward direction in the tooth bore.

Cement is placed in the canal space and/or on the post. The post, which is of matching size to the bur used to shape the root canal space, is positioned into the canal. Cement vents easily as the smallest diameter of the post at the bottom enters the larger diameter of the root canal space. Venting occurs easily until the post is almost fully seated or at least until the lower section of the post engages the lower section within the canal space.

This invention also provides for posts having other features used on posts including extensions, cutting extensions, threads, interrupted threads, through slots, venting slots, indentations, a disk at the top of the post which is positioned on the top of a tooth, used with indentations created in the root canal walls, or the like.

BRIEF DESCRIPTION OF THE DRAWINGS

FIG. 1 is a cross sectional view of the post and of this invention.

FIG. 2 a cross sectional view of the bur used with the post of FIG. 1.

FIG. 3 is a cross sectional view of the prepared root stub required for the post of FIG. 1.

FIG. 4 is a cross sectional view of the post of FIG. 1 positioned in the root stub of FIG. 3.

FIG. 6A is in a root stub.

FIG. 23 is a cross sectional view of an alternative post of this invention.

FIG. 24 is a cross sectional view of a bur used with the post of FIG. 23.

FIG. 25 is a cross sectional view of the post of FIG. 23 in a prepared root stub.

FIG. 26 is a side view of an alternative post of this invention.

FIGS. 26A, 26B, 26C and 26D illustrate various cross-sections for the post of FIG. 26.

FIG. 27 and 27A are cross sectional views of an alternative bur of this invention.

DESCRIPTION OF SPECIFIC EMBODIMENTS

Figure 5:
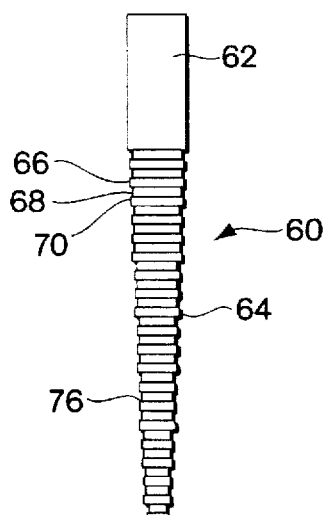
FIG. 5 is a side view of an alternative post of this invention.

The dental post of this invention includes a top section and a lower section. The top section is designed in any of the usual manners to include flanges, through splits, matching cores, wings, irregular shapes or the like. The lower section is designed to have at least two subsections. The effective diameter of the subsections decreases in the vertical direction away from top section. That is, the effective diameter of a subsection is less than the effective diameter of all the subsections above it. The subsections can have straight surfaces or curved including parallel surfaces, conical surfaces, circular surfaces of the like. The result of having the effective subsection diameter decrease in the vertical direction away from the top section is that the lower section tapers inwardly to avoid wedging effect on the tooth bore wall. Decreasing the effective diameter of the lower section of the post allows for conservation of more tooth structure, greater root strength and, therefore, less chance of root fracture and tooth loss. The subsections of the post are shaped so that the lower most portion of the subsection has a diameter larger than a diameter of a bottom of a root canal subsection. This permits the post subsection to match to a step of the root canal subsection rather than being positioned to exert a wedging force when downward force is exerted on the post. When the lower most portion bypasses a step, it will exert a wedging force during use. Thus, for example, a subsection having a conical section with the apex of the section comprising the lower most portion and the base of the section comprising the uppermost portion is not useful herein. Such a subsection would exert a wedging action during use since the post would be forced downward thus subjecting the step to an increased diameter portion of the post. (See FIG. 33) The lower section of the post can have any cross sectional shape such as triangular, square, rectangular, oval, or the like.

The root canal is prepared with a bur which allows placement of the post and conservation of tooth structure by matching the design of the post such that the lower section of the bur is smaller than the upper section. The bottom most portion of the bur is shorter than the matching portion of the post. The bottom most portion of the bur being shorter than the post eliminates any subsection of the post from engaging the matching root subsection below it and causing intense force which could lead to fracture. The walls of the post and the shaped walls of the root canal are designed so that force applied to the top of the post will not generate wedging forces that cause root fracture. There are many combinations of shapes of subsections of the lower sections of the post and matching sections of the shaped walls of the canal which avoid wedging forces. This invention eliminates the use of a tapered post matching a tapered section of a shaped root canal wall thereby eliminating the establishment of wedging forces when the post is positioned in the root canal.

In another embodiment, the lower section of the post has cutting extensions which cut a path and slot in the dentin and remain embedded in the dentin for retention. The top section can be provided with a preattached core. The post can be covered with enough extensions, such as aluminum oxide or diamond coating, to cut its own path in the root structure.

In another embodiment, the post includes an attached a full or partial flange. Holes in the flange can be provided for placement of matching sized pins.

In still another embodiment, the post includes a through slot up or down with extensions which match to indentations formed in the root canal by a special bur.

In still another embodiment, the post includes a through slot up or down with extensions which cut their own indentation into the dentin of root canal space.

In still another embodiment, the lower section of the post is threaded.

Referring to FIG. 1 though FIG. 4, a dental post 2, bur 20 and tooth stub 40 is shown. Dental post 2 has top section 4 which extends above a root canal space and lower section 6 which is placed into a root canal. Lower section 6 of post 2 has subsection 12, with parallel walls 8 and 10 subsection 14, subsection 16 and subsection 18 each designed such the diameter of a subsection is smaller than the subsections above it. The lowermost surface 11, 13 and 15 respectively of post subsection 12, 14 and 16 have a larger diameter than the diameter of steps 47, 49 and 51 respectively which comprises the bottom root canal subsection 42, 44 and 46 respectively. The bottom most subsection 18 of post 4 is longer than the matching subsection 36 of bur 20. When post 4 is positioned into root canal space 52, lower surface 9 contacts bottom surface 35 of root canal space 52. The increased length of subsection 18 of post 4 as compared to the bottom subsection of prepared canal subsection 48 results in the lowermost surface 11, 13 and 15 respectively of post subsection 12, 14 and 16 having a larger length than the lengths of subsections 46, 44 and 42 respectively so that the bottom root canal surfaces 47, 49 and 51 of tooth 50 respectively do not engage the surfaces 11, 13 and 15 . Thus, concentrating forces which could cause root fracture on the surfaces 47, 49 and 51 are eliminated. The increased length of subsection 18 of post 4 as compared to subsection 36 of bur 20 is as small as 20 microns, which is the thinnest cements can be pressed to or as large as slightly less than the height of a single subsection. For example, if subsection 16 of post 4 were 2 millimeters long, the bottom most subsection 18 of post 4 could be 1.9 millimeters longer for a total 3.9 millimeters. The matching bur 20 would have a lowest subsection 36 at 2 millimeters which would allow 0.1 millimeters of subsection 16 of post 4 to fit into matching prepared root subsection 46 of root 40. Surface 7 is the top of post 2 and surface 9 is the lower of post 2. Bur 20 has top section 22 which allows junction to a dental drill and lower section 24 which shapes root canal space 52 having steps 47, 49 and 51 in root stub 40 which comprise the bottom of root canal subsection 42, 44 and 46 respectively. Lower section 24 of bur 20 is further divided into subsection 30, subsection 32, subsection 34 and subsection 36 which are similar in diameter to subsection 12, subsection 14, subsection 16 and subsection 18 of post 2 respectively such that when bur 20 is placed into canal space 52 of root stub 40 it shapes canal space 52 resulting in subsection 42, having parallel walls 54 and 56 subsection 44, subsection 46 and subsection 48 to allow placement of post 2. It is preferred that subsection 12, subsection 14, subsection 16 and subsection 18 on post 2 and subsection 42, subsection 44 subsection 46 and subsection 48 of root stub 40 have parallel sides and be in close proximity for maximum retention.

Referring to FIG. 5 through FIG. 9, post 60 has top section 62 and tower section 64. Lower section 64 has representative subsection 66, subsection 68 and subsection 70. Subsection 66 and subsection 70 are larger in diameter than is subsection 68. Cement fills the resulting space for better retention. The average diameter at section 66 through section 70 is larger than the average diameter of the sections surrounding section 76.

Figure 6:
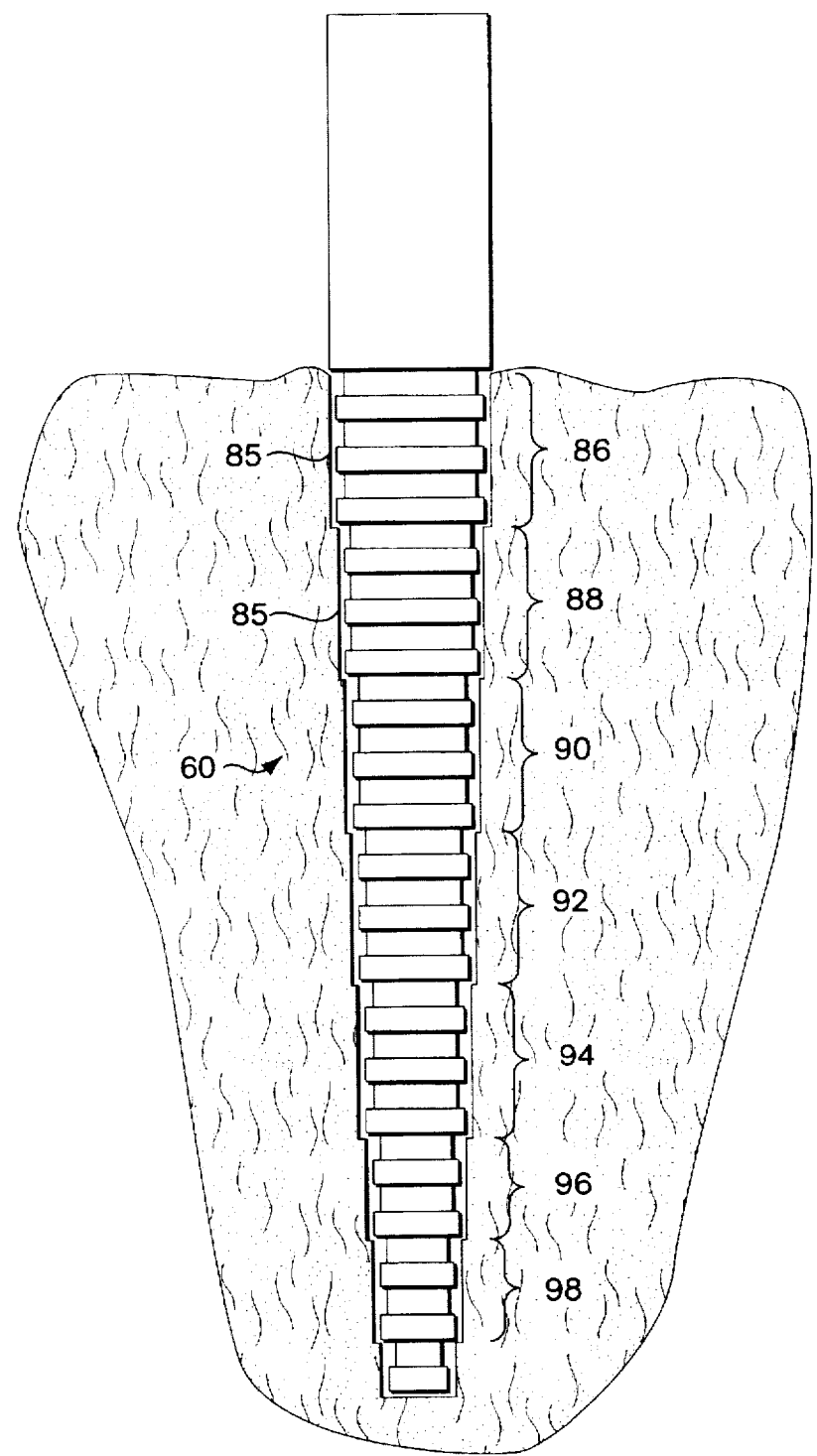
FIG. 6 and 6A is a side view of the post of FIG. 5 in a cross sectional view.
Figure 6A:
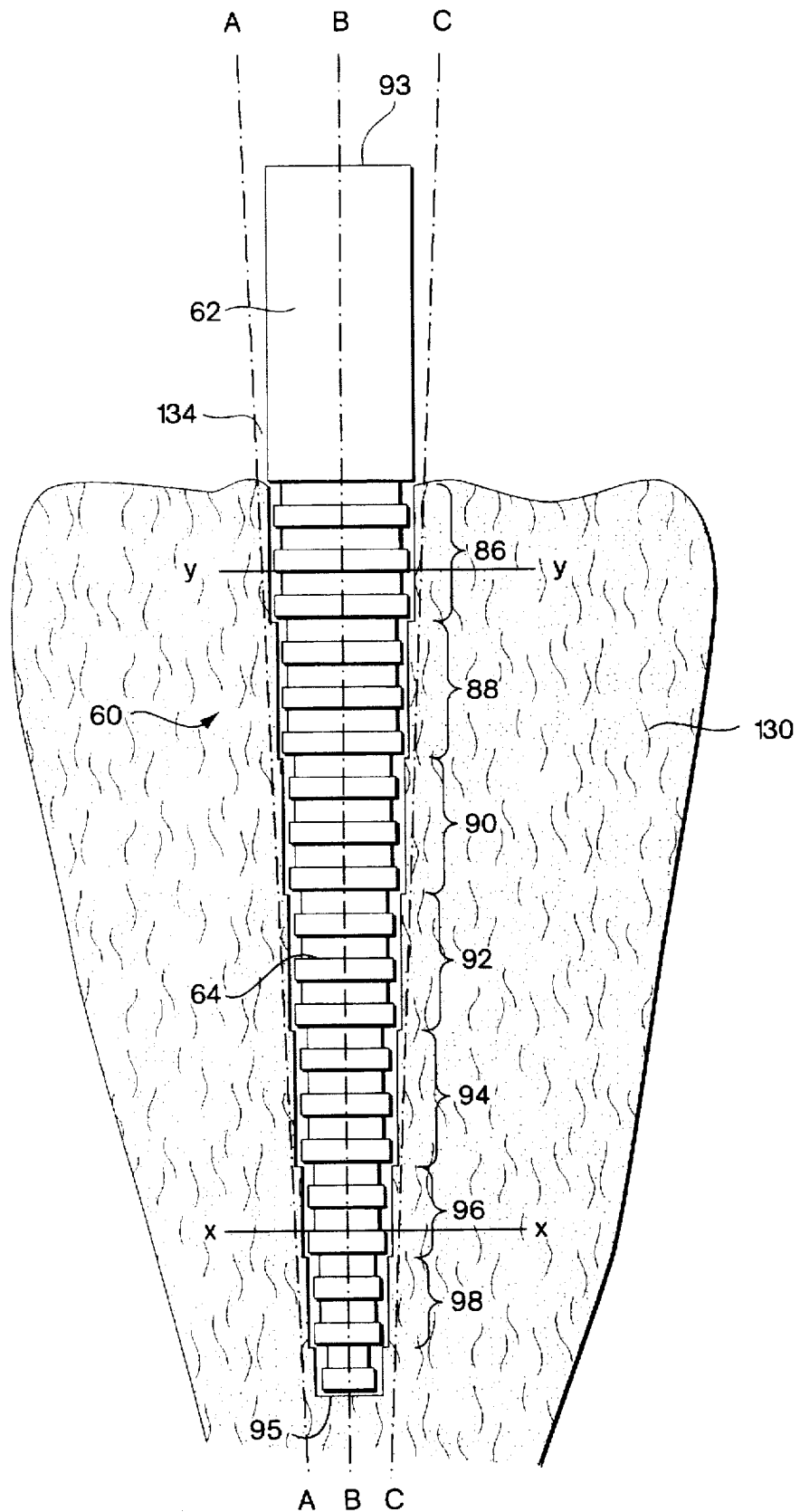

Referring to FIG. 6 and 6A, post 60 is positioned into root canal space 134 of root stub 130. As shown in FIG. 6, each subsection on the lower section is stepped. Lower section 64 of post 60 is designed such that the average diameter is decreasing from top to lower such that surface 93 is the top and surface 95 is the lower. The decrease in diameter is reflected by the tapering relationship of tangent line A—A relative tangent line C—C with central axis B—B being the long axis. The diameter from line A—A to line C—C through line Y—Y is greater than the diameter from line A—A to line C—C through lower line X—X Even though tangent line A—A and tangent line C—C provides a tapered shape, the individual subsection 86, subsection 88, subsection 90, subsection 92, subsection 94, subsection 96 and subsection 98 of root canal space 134 provides parallel surfaces such that no wedging occurs against canal wall 85 and consequently fracturing forces can be generated. The average diameter of each subsection is less than the average diameter of the subsections above it. For example, the average diameter of subsection 90 is less than the average diameter of subsection 86 or subsection 88.

Figure 7:
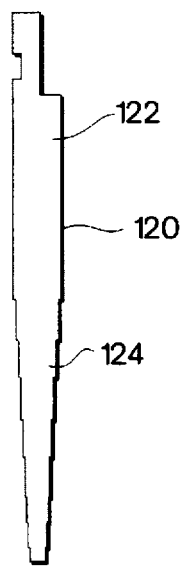
FIG. 7 is a cross sectional view of the bur used in conjunction with the post of FIG. 5.
Figure 8:
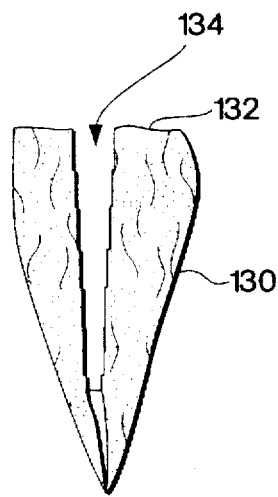
FIG. 8 is a cross sectional view of a prepared root stub used with the post of FIG. 5.
Figure 9:
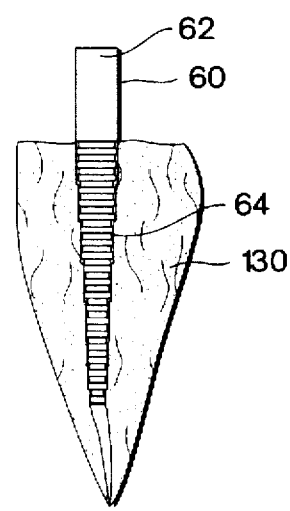
FIG. 9 is a side view of the post of FIG. 5 positioned in a cross sectional view of the root of FIG. 8.

Referring to FIG. 7, 8 and 9, Bur 120 has top section 122 which fits into a dental drill and lower section 124 which is placed into root canal space 132 to shape canal wall 85. Post 60 has lower section 64 which is positioned into root canal space 134 of root stub 130.

Figure 10:
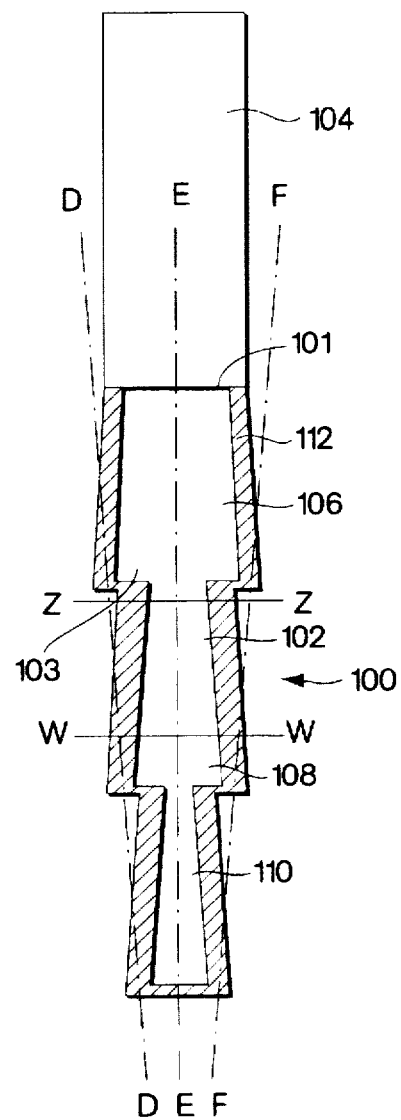
FIG. 10 is a cross sectional view of an alternative post of this invention.

Referring to FIG. 10, post 100 has top section 104 and lower section 102 which has conical subsection 106, subsection 108 and subsection 110. Lower section 102 is surrounded by cement 112. The apex 101 of conical subsection 106 is closer to the top section 104 than base 103. Subsection 106, subsection 108 and subsection 110 of post 100 are shape as cones with the top portion of the cone having a diameter smaller than the diameter of the bottom portion of the cone to demonstrate the concept of decreasing average diameter. The configuration of the changing diameter of the cones increasing from the top to the bottom but having a largest diameter smaller than the largest diameter of the next above, adjacent cone and other cones above the cone. Even though subsection 106, subsection 108 and subsection 110 are increasing in diameter individually the overall diameter is decreasing as shown by tangent line D—D and tangent line F—F, drawn tangent to the largest diameter of the cones, with line E—E being the long axis. Section 102 has a smaller diameter through line Z—Z than through line W—W, however, the average diameter is determined where line Z—Z intersects tangent line D—D and tangent line F—F which is larger than the diameter determined by lower line W—W determined by where it intersects tangent line D—D and tangent line F—F.

Figure 11:
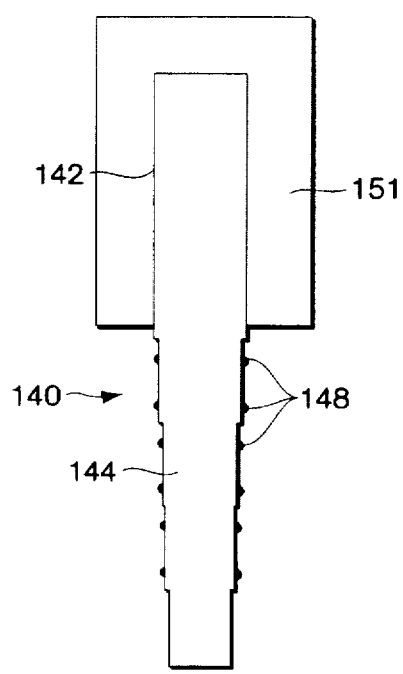
FIG. 11 is a cross sectional view of an alternative post of this invention.
Figure 12:
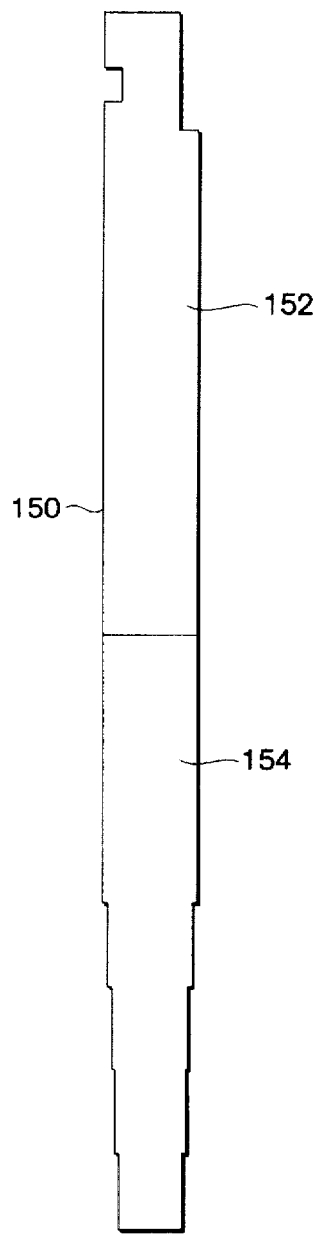
FIG. 12 is a cross sectional view of a bur used with the post of FIG. 11.
Figure 13:
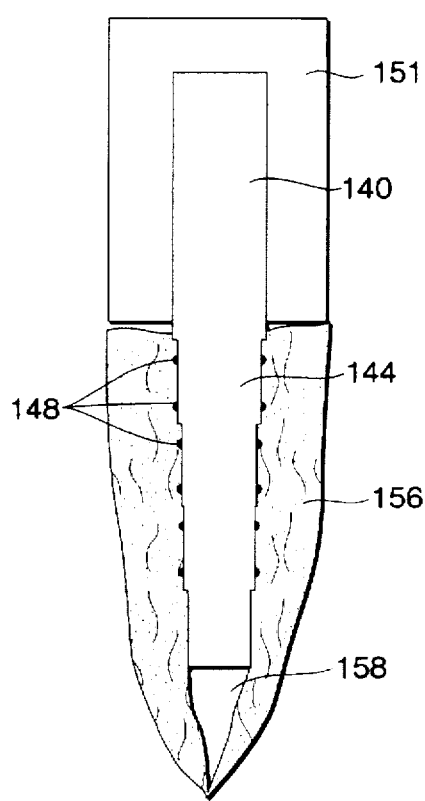
FIG. 13 is a cross sectional view of the post of FIG. 11 in a prepared root stub.

Referring to FIG. 11 through FIG. 13, post 140 has top section 142 with preattached core 151 made of the same material as the post, metal such as gold, stainless steel, titanium or the like, or softer dental materials such as porcelain, composite, metal composite combinations or the like, and lower section 144 with cutting extensions 148. Bur 150 of FIG. 12, has top section 152 which attaches into a dental drill and lower section 154 which prepares the root canal space 158. After bur 150 prepares the root canal space 158 of root 156, post 140 is position into root canal space 158 such that cutting extensions 148 cut pathways and slot into root structure for retention. If many cutting extensions 148 are used, post 140 cuts its own path and hole into root canal space 158 and eliminates the need for bur 150. The post can cut its own path with the aid of having an upper portion which attaches to a drill, handle, pliers, hemostats of the like.

Figure 14:
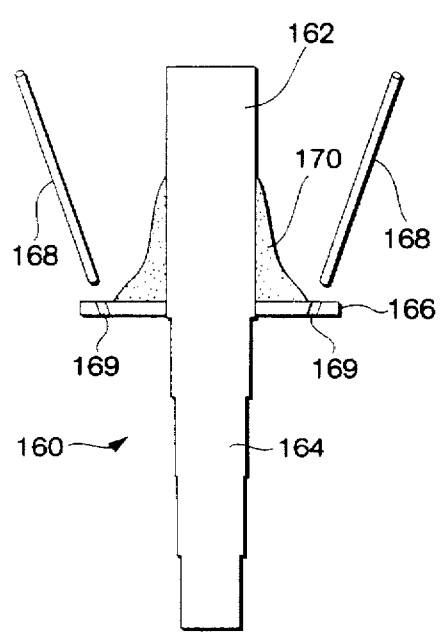
FIG. 14 is a cross sectional view of an alternative post of this invention.
Figure 15:
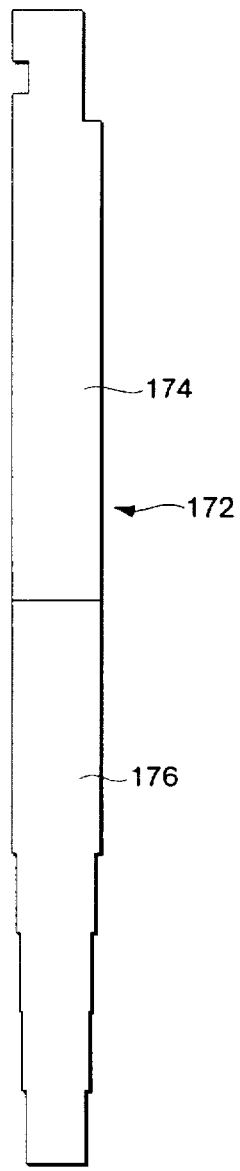
FIG. 15 is a cross sectional view of a bur used with the post of FIG. 14.
Figure 16:
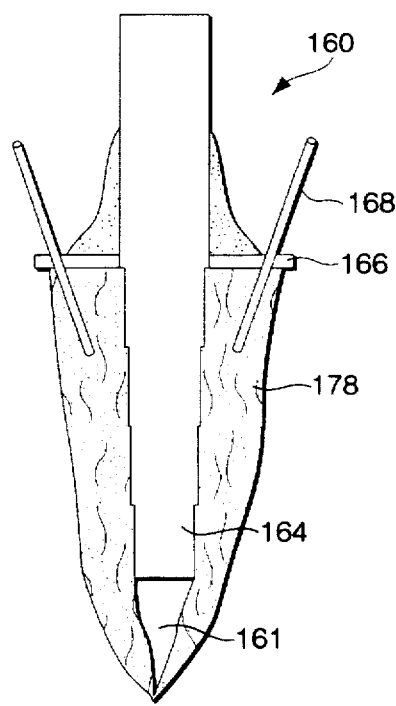
FIG. 16 is a cross sectional view of the post of FIG. 14 in a prepared root stub.

Referring to FIG. 14 through FIG. 16, post 160 has top section 162, lower section 164, flange 166, supports 170 and holes 169 though flange 166 for placement of pins 168. Bur 172 has upper portion 174 to attach to a dental drill and lower portion 176 to shape root canal space 161. After placement of post 160 into root canal space 161, a bur (not shown) drills holes through holes 169 of flange 166 and into dentin of root 178. Pins 168 are cement or screwed to place to provide resistance to rotational, lateral and dislodging forces.

Figure 17:
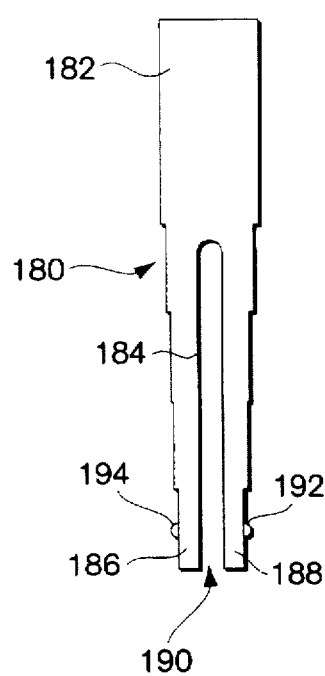
FIG. 17 is a cross sectional view of an alternative post of this invention.
Figure 18:
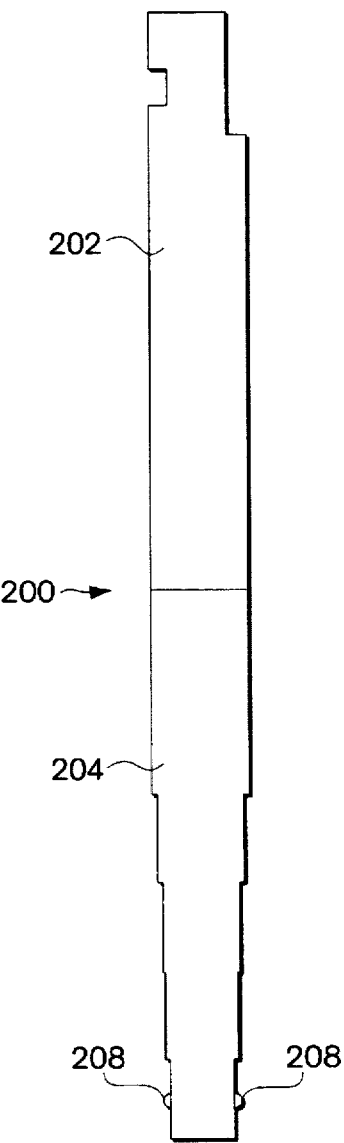
FIG. 18 is a cross sectional view of a bur used with the post of FIG. 17.
Figure 19:
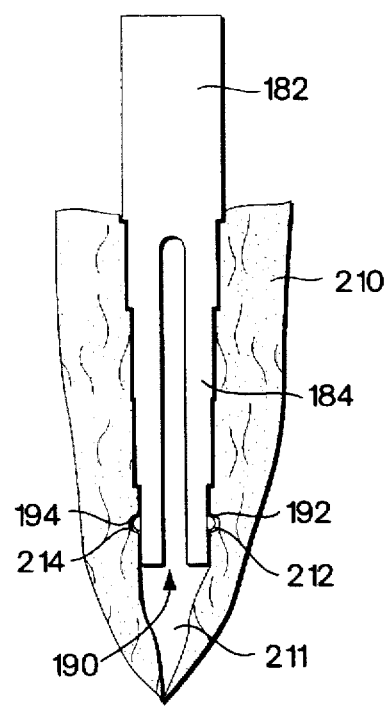
FIG. 19 is a cross sectional view of the post of FIG. 17 in a prepared root stub.

Referring to FIG. 17 through 19, post 180 has top section 182 and lower section 184. Lower section 184 has leg 186 and leg 188 with through split 190 and extension 192 and extension 194. Bur 200 has top section 202 which is shaped to be placed into a dental drill and lower section 204 with cutting ring 208. Bur 204 is smaller in diameter than the matching height diameter of post 180. Bur 200 drills down into position and is move laterally to form indentation 214 and indentation 212 into root canal space of tooth 210. Post 180 is place into root canal space 211, leg 186 and leg 188 compresses together by external compression such as dental pliers or through self compression as extension 194 and extension 192 engage tooth structure until fully seated such that extension 194 of post 180 engages indentation 214 of root canal space 211 and extension 192 of post 180 engages indentation 212 of root canal space 211. Extension 192 and 194 are not subsections as used herein since they extend into wall indentation rather than being positioned adjacent to the main canal wall. Through split 190 fills with cement which stops compression of leg 186 and leg 188 of post 180 such that extension 194 and extension 192 can not disengage from indentation 214 and indentation 212 of root canal space 211.

Figure 20:
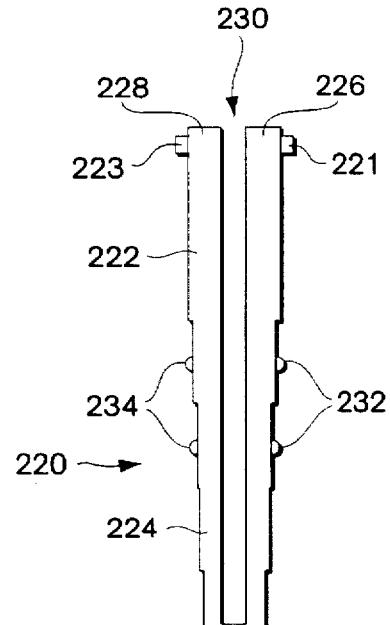
FIG. 20 is a cross sectional view of an alternative post of this invention.
Figure 21:
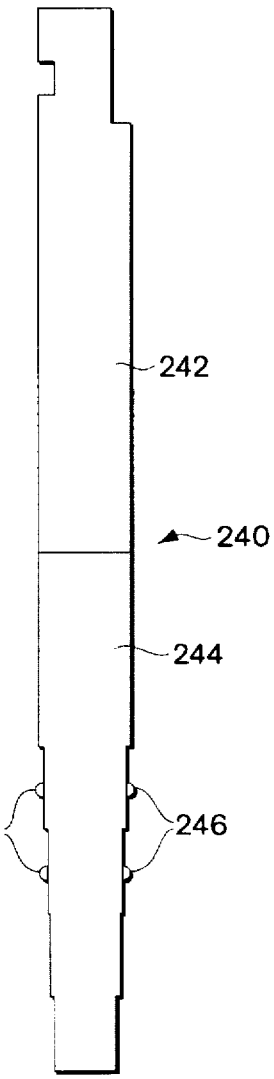
FIG. 21 is a cross sectional view of a bur used with the post of FIG. 20.
Figure 22:
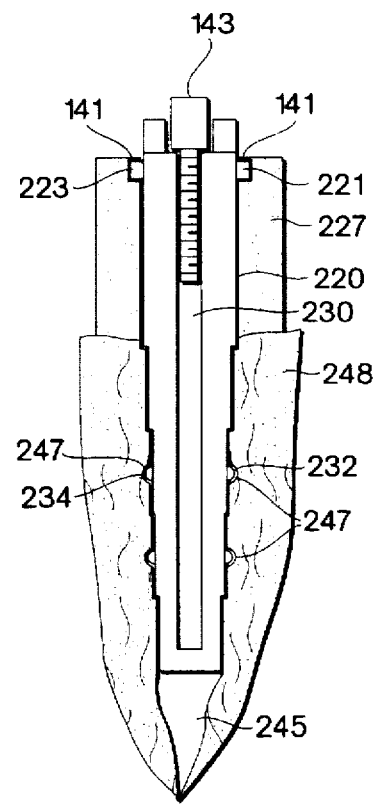
FIG. 22 is a cross sectional view of the post of FIG. 20 in a prepared root stub.

Referring to FIG. 20 through FIG. 22, post 220 has top section 222 which has leg 228 with extension 223, leg 226 with extension 221 and through split 230 and lower section 224 with extensions 232 and extensions 234. Similar to extension 192 and 194, extensions 232 and 234 are not subsections as that term is used herein. Bur 240 has top section 242 and lower section 244 with cutting rings 246. Bur 240 is positioned down into canal space 245 shaping the canal and is moved laterally to form indentations 247 in root canal space 245. Post 220 has leg 228 and leg 226 compressed together such that extensions 232 and 234 can enter into canal space 248. When fully seated leg 228 and leg 226 are released which positions extensions 232 and 234 of post 220 into indentations 247 of root canal space 245. Core 227 is positioned over post 220 by compressing legs 226 and 228 such that extensions 223 fit into core 227 and engage slots 141 on core 227 to provide retention. Through split 230 is filled with cement, left open or filled with key 143.

Referring to FIG. 23 through 25, post 250 has top section 252 with attachment for a screw driver 255 and lower section 254 with threads. Bur 258 has top section 260 for placement into a dental drill and lower section 262 for shaping of root canal space 263. After root canal space 264 is shaped by bur 258, post 250 is threaded into position. Post 250 can be designed such the size of the thread do not engage root canal walls until the final step is reached and therefore minimizing the numbers of turns for complete placement. Threads provided additional retention to the previously discussed step down parallel designs.

Referring to FIG. 26, post 270 has top section 272 and lower section 274. Cross sections of post 270 is round, oval, rectangular, square, triangular or the like as observed from cross section L—L as shown by oval 280, square 282, triangle 284 or circle 276 with venting grooves 278. Post 270 is one uniform cross section or has multiple cross section variations in the same post.

Referring to FIG. 27 and 27A, bur 290 has top section 292, cutting area 294, non cutting end 296 which guides the bur down a root canal so it can not drill out the side of a tooth and non cutting areas 298 for provide for no tipping of bur 290. Alternative non cutting end 295 and indented non cutting area 293 of bur 291 provides guidance but allows lateral movement as is required when indentations in root canal walls is done.

Figure 28:
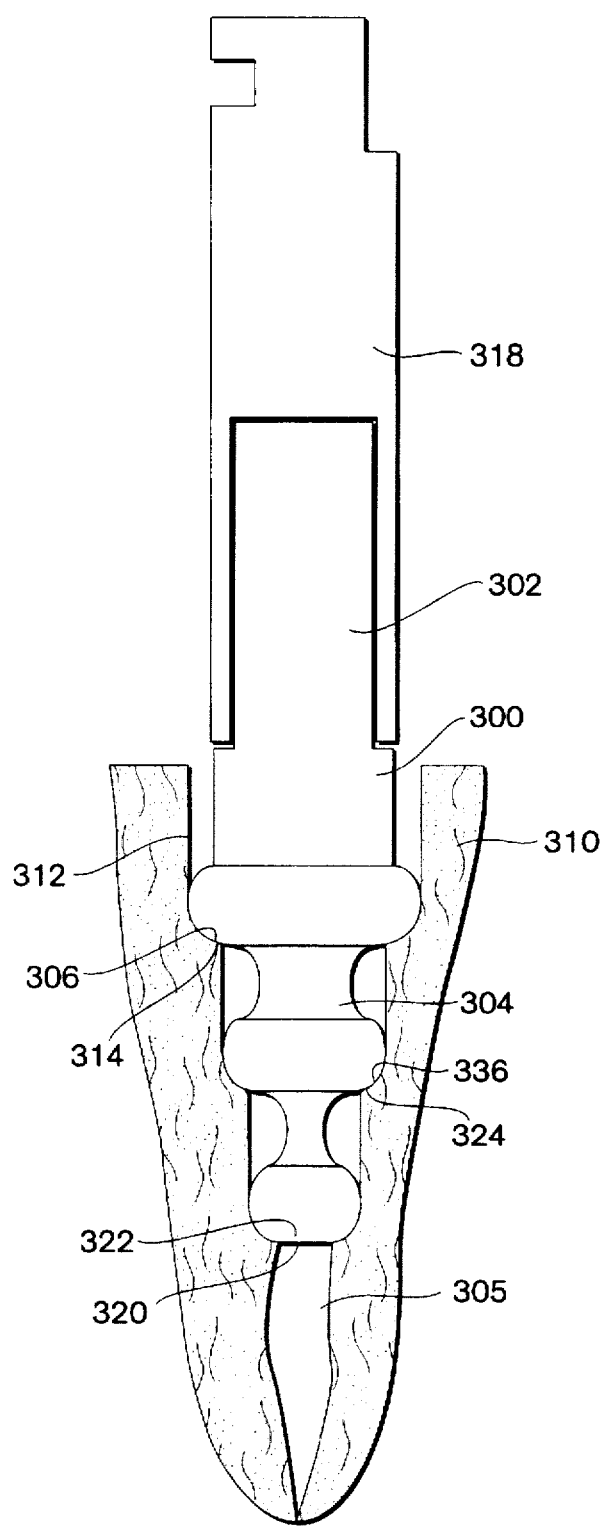
FIG. 28 is a cross section view of an alternative post of this invention.

Referring to FIG. 28, post 300 has top section 302 which has means to attachment a removable drill attachment, handle, pliers or the like, lower section 304 which is cutting similar to a bur design. Post 300 is placed in post holder 318 which is place into a dental drill. Holder 318 allows drilling with post 300 which shapes root canal space 305 forming its own hole 312. Post 300 is cemented to place by either placing cement into root canal space 305 prior to drilling or preferably by removing post 300 after initial shaping, cleaning debris, and applying cement to post 300 or into root canal space 305. Post 300 is positioned into root canal space 305, any more drilling is accomplished as required and post 300 is release from holder 318 and left in position. Post 300 provides flat areas such as surface 326 and 322 to resist downward forces against surfaces 324 and 320 of root 310.

Figure 29:
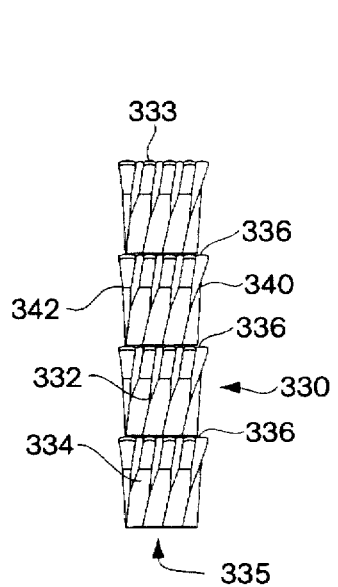
FIG. 29 is a side view of a section of an alternative post of this invention.

Referring to FIG. 29 a post subsection 330 is shown which has section 332 and 334 each of which has ledge 336 for added retention. To form ledge 336, wall 342 and wall 340 are tapered such that the diameter decreases toward the bottom 335 from top 333. A balance is achieved of potential wedge forces from tapered walls to added retention of ledges.

Figure 32:
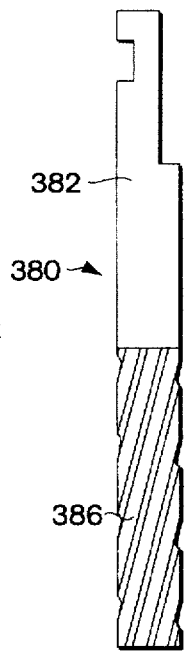
FIG. 32 is a side view of the prior art bur for forming the canal of FIG. 32A.

Referring to FIG. 32, a bur 380 has top section 382 which fits into a dental drill and lower section 386 which shapes the root canal to accept post 390. Bur 380 creates parallel canal wall 392 to minimize lateral force of tapered wall 394 of post 390 onto wall 392 of root canal space 406 when downward force is applied to the top of post 390. Post 390 is overall the same diameter from entrance into root canal space 406 of root 400 to the end as each subsection is the same size which results in close proximity and possible perforation at root wall 402.

Figures 30, 30A:
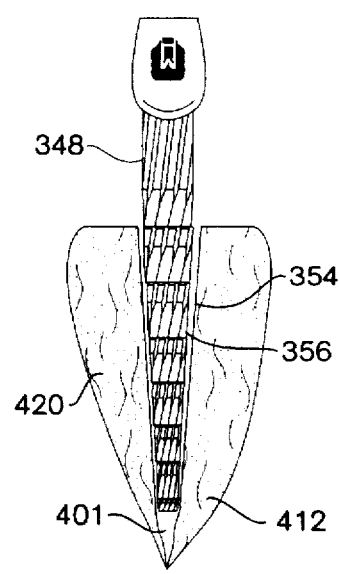
FIG. 30 is a side view of a tapered bur for forming the canal of FIG. 30A.
FIG. 30A is a side view of an alternative post of this invention.

Referring to FIG. 30, a bur 346 has top section 350 which fits into a dental drill and lower section 352 which is tapered to maintain maximum amount of tooth structure as root shaping is performed. Post 348 is placed into root canal space 401 after bur 346 has prepared it. Post 348 has subsections which get smaller toward the bottom of the post. There is more root structure remaining after root canal space 410 is prepared by bur 346 than is left if FIG. 32 after preparation of root canal space 406 with bur 380. The remaining root 420 of FIG. 30 has more remaining structure than root 400 of FIG. 32 and is stronger. In addition, the distance from post 348 to the outside wall 412 of root 420 is less and therefore there is less chance of perforation. However, tapered wall 356 of post 348 causes wedging force against tapered root canal wall 354 of root canal space 401 of root 420. The possibility of unrepairable fracture to root 420 of FIG. 30 is greater than the root 400 when equal force is applied downward onto the top of the post 348 of FIG. 30 and post 390 of FIG. 32A. Bur 346 can be used as a first bur to prepared a canal prior to preparation by drill 360 of FIG. 31. Bur 360 can be of a degree of taper which matches the relative degree of taper of a segmentally parallel post such as the degree of taper of line A—A and C—C described in FIG. 6A. The diameter of Bur 360 would than be decreased in diameter by the same amount as the difference of a decreased diameter of a subsection to the subsection below it. The result would be bur 360 would only engage root structure once it is matched in diameter which would be equal to one subsection. The amount and length of tooth reduction by bur 360 would be limited to the length of a single subsection.

Bur 346 of FIG. 30 can prepare a root prior to a post with cutting extensions which can cut its own post space. This would limit the amount of force required to place a self cutting post.

Figures 31, 31A:
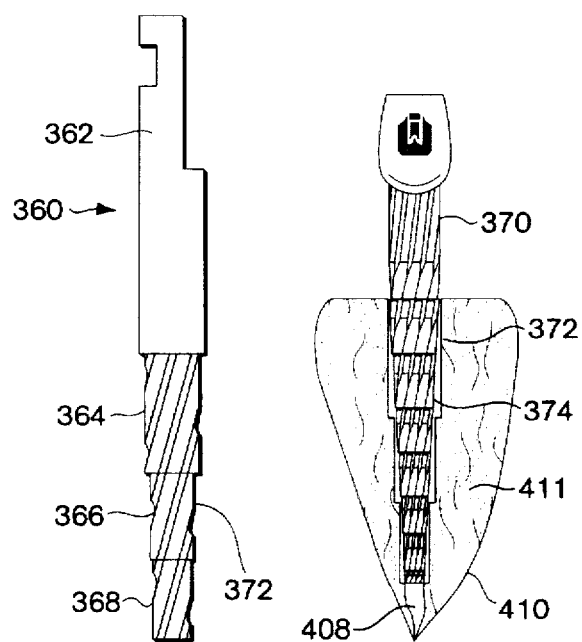
FIG. 31 is a side view of a bur of this invention.
FIG. 31A a side view of an alternative post of this invention.
Figure 32A:
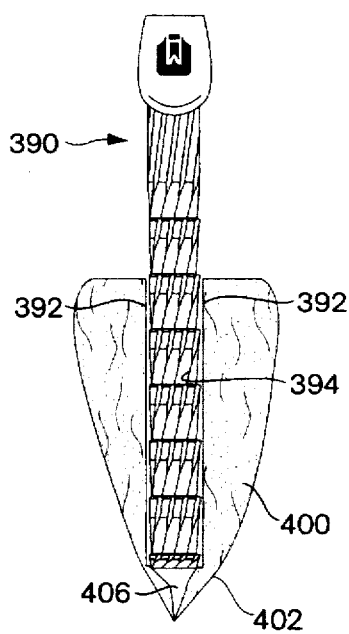
FIG. 32A is a side view of a prior art post for comparison with this invention.

Referring to FIGS. 31 and 31A, bur 360 has top section 362 shaped to fit into a dental drill and lower section 372. Lower section 372 has subsection 364, subsection 366 and subsection 368 which shapes root canal space 408 of root 411. The bur is important because it creates non tapered walls which minimizes the effects tapered walls on a post produces resulting in wedging force on canal walls. Post 370 of FIG. 31A having subsection 374 is the same design as post 348 of FIG. 30. The theory is reinforced by the resulting non tapered shape of canal 406 in FIG. 32 which minimizes the wedging effects of tapered walls 394 of post 390 when downward force is applied to post 390.

There is more loss of tooth structure with use of bur 360 of FIG. 31 than bur 348 of FIG. 30 but decreased loss of tooth structure than after use of bur 382 of FIG. 32. Bur 30 of FIG. 30 creates tapered canal walls and therefore, more likelihood of catastrophic root fracture. Bur 360 of FIG. 31 and bur 380 of FIG. 32 creates parallel canal walls which decreases the likelihood of root fracture. Bur 360 produces a root canal space shape which minimizes root fracture because it creates parallel canal walls and conserves tooth structure.

Figure 33:
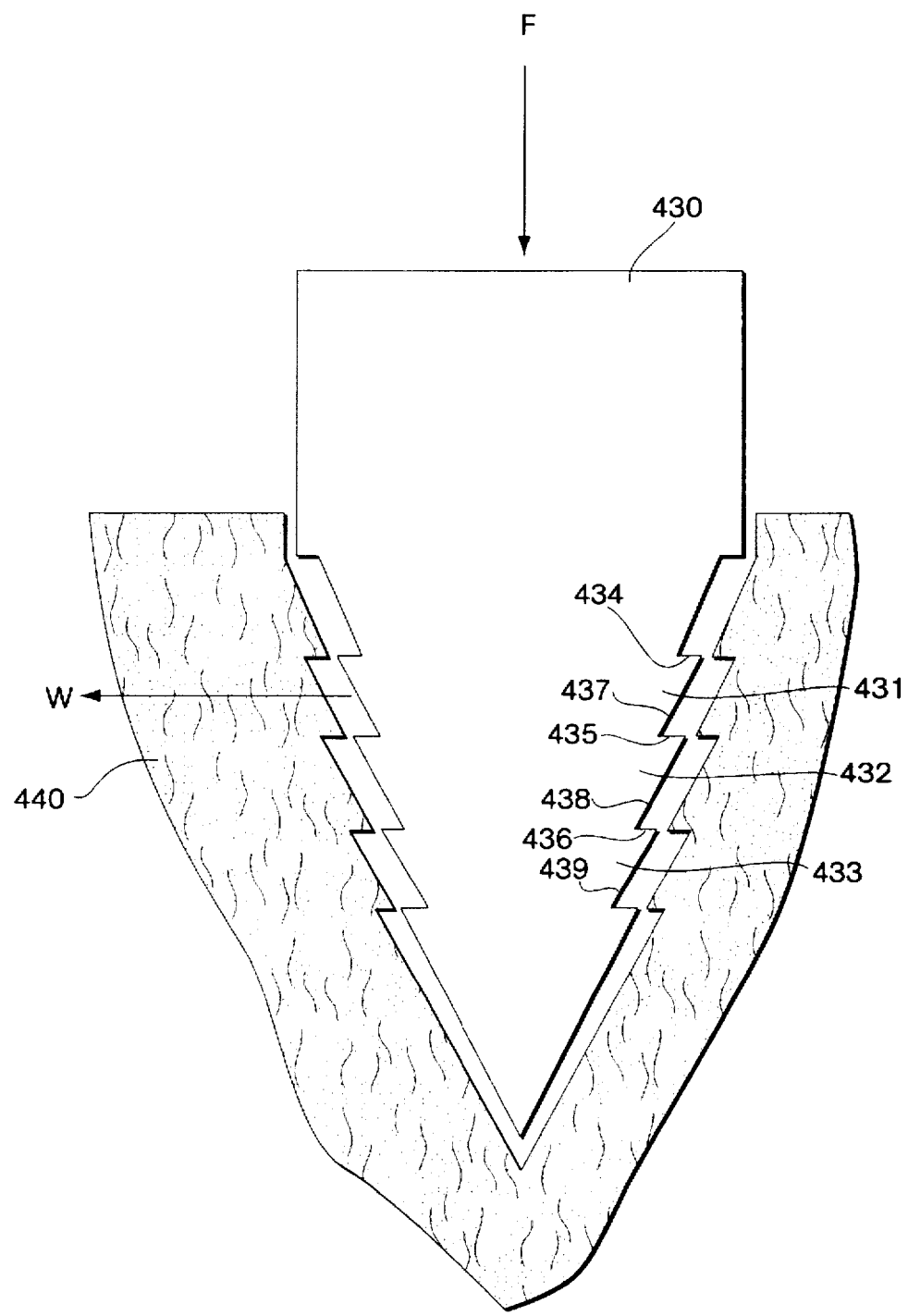
FIG. 33 shows a prior art post.

FIG. 33 illustrates the wedging forces exerted by a prior art post. The post 430 has conical subsection 431, 432 and 433. Each conical subsection 431, 432, and 433 has an uppermost base 434, 435 or 436 and a lowermost apex 437, 438 or 439. When a downward vertical force F is exerted on post 430, a wedging force W is exerted on the tooth 440 which tends to fracture the tooth. The wedging force W is caused by downward movement of an increasing diameter of the post 430. This contrasts, for example, with the post of FIG. 10 where a downward force on the post, tends to reduce the post diameter to which the canal all is exposed.

I claim:

1. A dental post shaped to be positioned within a bore of a tooth which comprises:

a top section a lower section attached to said top section, said lower section being formed from a plurality of post subsections having an effective diameter, the effective diameter of the subsections decreasing in a vertical direction away from said top section such that the overall surface of the lower section tapers inwardly toward a central axis of said lower section, each of said post subsections having a lowermost surface with a diameter larger than a diameter of a root canal subsection adjacent said lower-most surface and a bottom-most subsection having a length which prevents contact of a lowermost surface of each post subsection with a wall of said bore when said post is inserted into said bore.

2. The dental post of claim 1 wherein walls of each subsection are parallel.

3. The dental post of claim 1 wherein a surface of each subsection are conical having an apex and a base wherein said apex is positioned nearer said top section than said base.

4. The dental post of claim 1 wherein walls of each subsection are stepped and parallel.

5. The dental post of any one of claims 1,2,3 or 4 wherein cutting extensions are positioned on walls of said subsections.

6. The dental post of any one of claims 1,2,3 or 4 having a flange secured to said top section, said flange having at least one hole and a pin extending through said hole at an angle relative to said central axis.

7. The dental post of any one of claims 1,2,3 or 4 having a slot extending the length of said lower section and at least one extension on a wall of a subsection.

8. The dental post of any one of claims 1,2,3 or 4 having a slot extending the length of said top section and a lower section and at least one extension on a wall of a subsection.

9. The dental post of any one of claims 1, 2, 3 or 4 wherein threads are positioned on walls of at least one said subsection.

* * * * *